United States Patent
Modi

(10) Patent No.: US 11,166,912 B2
(45) Date of Patent: Nov. 9, 2021

(54) ORALLY ADMINISTRABLE COMPOSITION

(71) Applicant: Pankaj Modi, Ancaster (CA)

(72) Inventor: Pankaj Modi, Ancaster (CA)

(73) Assignee: CTT Pharma Inc., Ontario (CA)

( * ) Notice: Subject to any disclaimer, the term of this patent is extended or adjusted under 35 U.S.C. 154(b) by 0 days.

(21) Appl. No.: 15/059,444

(22) Filed: Mar. 3, 2016

(65) Prior Publication Data
US 2017/0252300 A1 Sep. 7, 2017

(51) Int. Cl.
| | |
|---|---|
| *A61K 9/107* | (2006.01) |
| *A61K 31/352* | (2006.01) |
| *A61K 9/00* | (2006.01) |
| *A61K 31/485* | (2006.01) |
| *A61K 31/4468* | (2006.01) |
| *A61K 9/70* | (2006.01) |
| *A61K 31/05* | (2006.01) |

(52) U.S. Cl.
CPC ............ *A61K 9/1075* (2013.01); *A61K 9/006* (2013.01); *A61K 9/0053* (2013.01); *A61K 9/7007* (2013.01); *A61K 31/05* (2013.01); *A61K 31/352* (2013.01); *A61K 31/4468* (2013.01); *A61K 31/485* (2013.01)

(58) Field of Classification Search
CPC .................................................... A61K 31/05
See application file for complete search history.

(56) References Cited

U.S. PATENT DOCUMENTS

| | | | | |
|---|---|---|---|---|
| 5,989,583 | A * | 11/1999 | Amselem | A61K 9/145 424/439 |
| 6,350,458 | B1 * | 2/2002 | Modi | A61K 9/0043 424/400 |
| 6,849,263 | B2 * | 2/2005 | Modi | A61K 9/0019 424/400 |
| 8,623,401 | B2 * | 1/2014 | Modi | A61K 9/0056 424/441 |

FOREIGN PATENT DOCUMENTS

| | | |
|---|---|---|
| CA | 2268187 | 4/1998 |
| CA | 2229286 | 8/1999 |
| CA | 2354148 | 6/2000 |
| CA | 2382535 | 3/2001 |
| CA | 2428535 | 6/2002 |
| CA | 2624110 | 11/2010 |
| WO | 2001/722728 A2 | 10/2001 |
| WO | 2004/043445 A1 | 5/2004 |
| WO | 2007/062494 A1 | 6/2007 |
| WO | 2009/015456 A1 | 2/2009 |
| WO | 2010/002418 | 1/2010 |
| WO | 2013/009928 A1 | 1/2013 |
| WO | 2015/068052 A2 | 5/2015 |

OTHER PUBLICATIONS

European Search Report—dated Oct. 25, 2019—EP Application No. 17759030.4—CTT Pharma Inc.

* cited by examiner

*Primary Examiner* — Sarah Alawadi
(74) *Attorney, Agent, or Firm* — Susan Tandan; Gowling WLG (Canada) LLP

(57) ABSTRACT

An orally administrable micellar composition is provided. The composition comprises a pharmaceutical agent encapsulated in micelles formed by at least one micelle-forming compound in a pharmaceutically acceptable aqueous solvent comprising an alkali metal salicylate and a pharmaceutically acceptable edetate combined with at least one physiologically acceptable film forming agent.

14 Claims, 3 Drawing Sheets

ORALLY ADMINISTRABLE COMPOSITION

FIELD OF THE INVENTION

The present invention generally relates to an orally administrable composition, and more particularly, to an orally administrable composition comprising a nanonized therapeutic.

BACKGROUND OF THE INVENTION

Despite significant efforts in academic and commercial laboratories, major breakthroughs in oral peptide and protein formulation have not been achieved. In addition, relatively little progress has been made in developing safe and effective oral formulations for cannabinoids and derivatives. Major barriers to developing oral formulations for cannabinoids and derivatives include poor intrinsic permeability, lumenal and cellular enzymatic degradation, rapid clearance, and chemical instability in the gastrointestinal (GI) tract. Approaches effective to address these barriers in formulations comprising small, organic drug molecules, are not readily applied to formulations including large therapeutic molecules such as proteins or cannabinoids.

Scientists have explored various administration routes for cannabinoids and derivatives, other than the injection, including oral, intranasal, rectal and vaginal for the effective delivery of large molecules. Oral and intranasal delivery are of interest because the oral and nasal membranes offer advantages over other routes of administration. For example, drugs administered through these membranes have a rapid onset of action, provide therapeutic plasma levels, avoid first pass effect of hepatic metabolism, and avoid exposure of the drug to the hostile GI environment. Additional advantages include easy access to the membrane sites providing for easy application, localization and removal of the drug. Further, these membranes provide the potential for prolonged delivery of large molecules.

Oral administration routes for large molecules has received far more attention than other administrable routes. In addition, to the fact that the oral cavity is easily accessible and convenient, oral membranes such as the sublingual mucosa and the buccal mucosa, are relatively permeable, thereby providing ready absorption of orally administered drugs, and thus, acceptable bioavailability. The ability of molecules to permeate through the oral mucosa appears to be related to molecular size, lipid solubility and charge. Small molecules, less than 1000 daltons, appear to cross the mucosa readily. As molecular size increases, molecular permeability decreases. Lipid soluble compounds are more permeable than non-lipid soluble molecules. Further, neutral or non-ionized molecules exhibit greater absorption than charged molecules.

While some penetration enhancing products have been determined to facilitate mucosal administration of large molecule drugs, very few such enhancers have been approved for market use due to lack of a satisfactory safety profile, lowering of mucosal barrier function, impairment of the mucocilliary clearance protective mechanism, and irritant properties. In addition, penetration enhancers are extremely bitter and unpleasant in taste. Several approaches have been utilized to improve the taste of enhancers, but none have been approved for human consumption to date.

Thus, it would be desirable to develop a formulation effective for the delivery of therapeutic compounds, for example, large therapeutic molecules such as proteins or cannabinoids.

SUMMARY OF THE INVENTION

A novel composition has now been developed which is effective for the oral delivery of a large therapeutic compound. The composition comprises at least one physiologically acceptable film forming agent combined with the therapeutic molecule encapsulated in a micellar composition.

Thus, in one aspect of the invention, a composition is provided comprising at least one physiologically acceptable film forming agent combined with a pharmaceutical agent encapsulated in a micellar mixture comprising a micelle-forming compound in an aqueous solvent, an alkali metal salicylate and a pharmaceutically acceptable edetate.

In another aspect of the invention, a method of preparing an orally administrable micellar composition comprising a pharmaceutical agent is provided comprising the steps of:

i) admixing the selected pharmaceutical agent in a solvent with a first micelle-forming compound in an amount of from 1 to 10 wt./wt. % of the total composition, an alkali metal salicylate in an amount of from 1 to 10 wt./wt. % of the total composition, a pharmaceutically acceptable edetate in an amount of from 1 to 10 wt./wt. % of the composition, and optionally an isotonic agent, to form micelles;

ii) optionally adding to the micellar composition a second micelle-forming compound in an amount of from 1 to 10 wt./wt. % of the total composition, and further optionally adding a third micelle-forming compound to the micellar composition in an amount of from 1 to 10 wt./wt. % of the total composition, wherein the total amount of the micelle-forming compounds, alkali metal salicylate, edetate and isotonic agent, is less than 50 wt./wt. % of the composition, and mixing vigorously to form a mixed micellar composition; and iii) combining the micellar composition or mixed micellar composition with at least one physiologically acceptable film forming agent in an aqueous solvent to form a gel, spreading the gel into a thin layer and allowing the gel to set, optionally by applying cycles of heating and cooling.

These and other aspect of the invention are described in the detailed description and by reference to the following figures.

DETAILED DESCRIPTION OF THE INVENTION

Figure 1:
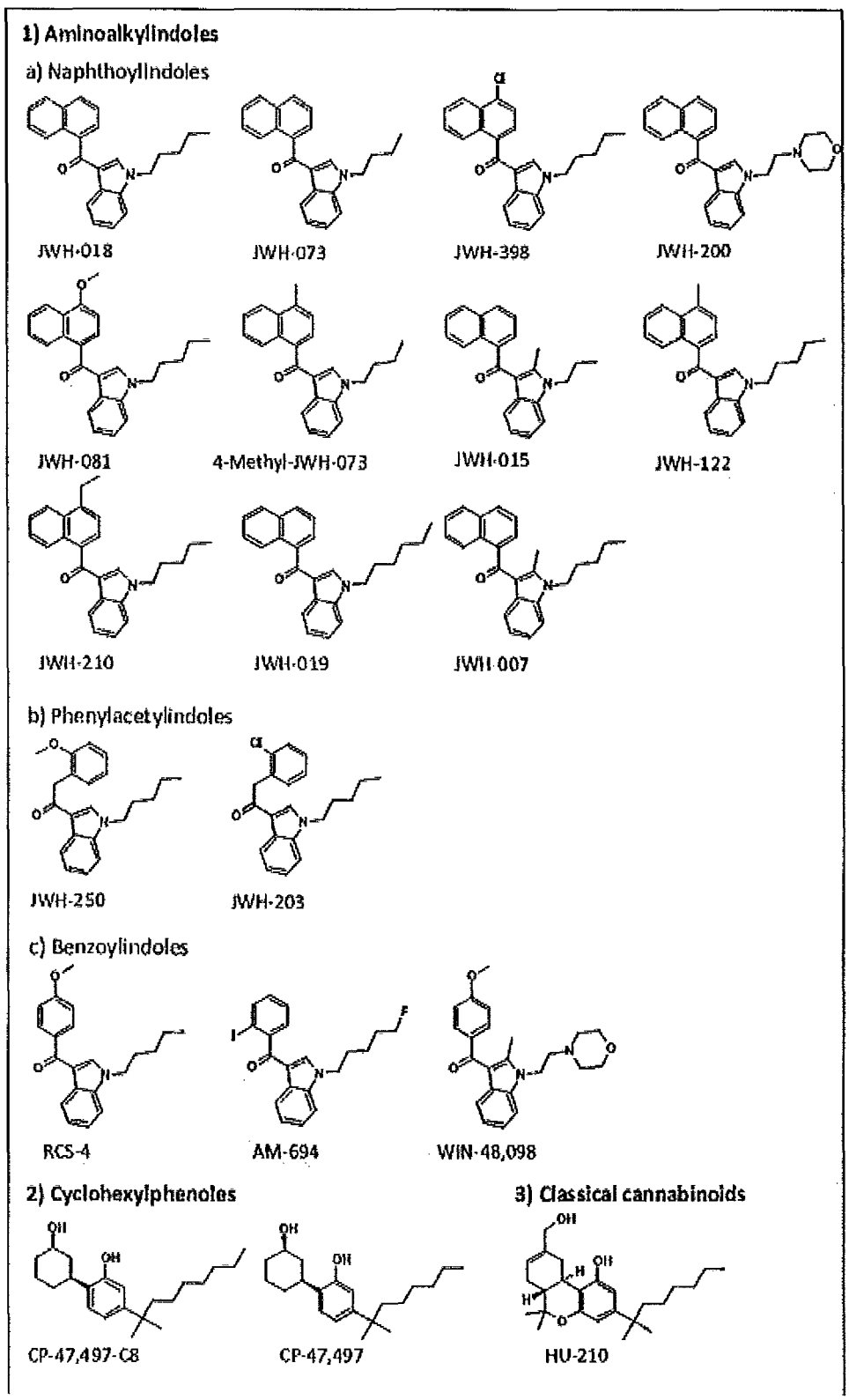
FIG. 1 illustrates chemical structures of cannabinoid compounds.

A composition is provided comprising at least one physiologically acceptable film forming agent combined with a pharmaceutical agent encapsulated in a micellar mixture comprising at least one micelle-forming compound in an aqueous solvent, an alkali metal salicylate and a pharmaceutically acceptable edetate.

The present composition comprises one or more micelle-forming compounds. As will be appreciated by those skilled in the art, a micelle is a colloidal aggregate of amphipathic molecules in which the polar hydrophilic portions of the molecule extend outwardly while the non-polar hydrophobic portions extend inwardly. Examples of micelle-forming compounds for use in the present composition include, but are not limited to, polyoxyethylene ethers, esters or alcohols; alkali metal alkyl sulfates, e.g. comprising a C8 to C22 alkyl, preferably C12 alkyl (lauryl) and any alkali metal, e.g. sodium or potassium, such as sodium lauryl sulphate; bile acids; lecithin, hyaluronic acid, pharmaceutically acceptable salts of hyaluronic acid, octylphenoxypolyethoxyethanol, glycolic acid, lactic acid, oleic acid, linoleic acid, linolenic acid, monoolein, monooleates, monolaurates, borage oil, evening of primrose oil, chamomile extract, cucumber extract, menthol, trihydroxy oxo cholanylglycine, glycerin, polyglycerin, lysine, polylysine, triolein, polidocanol alkyl ethers, chenodeoxycholate, deoxycholate, and mixtures thereof.

As used herein, the term "polyoxyethylene ethers" (also referred to as polyethylene glycols) includes, but is not limited to, any of several condensation polymers of ethylene glycol, for example, $HOCH_2$ ($CH_2OCH_2$), $CH_2OH$ ($OCH_2CH_2$), $H(OCH_2CH_2)$ or $OH$ ($OCH_2CH_2$) with average molecular weights from 200 to 6000. Also suitable are polyoxyethylene alcohols and esters. Examples of suitable compounds include Brij™ compounds, i.e., Brij™ 30, 52, 56, 58, 72, 76, 700, 721, 92, 93, 96, 97, 98, 99, etc. Polyoxyethylene ethers are preferred, and most preferred is polyoxyethylene 9-lauryl ether.

Examples of bile acids for use in the present composition include, but are not limited to, cholic acid, cholic acid derivatives such as deoxycholic, glycocholic, chenodeoxycholic, taurocholic, glycodeoxycholic and taurodeoxycholic acids, salts thereof and mixtures thereof. A preferred bile acid salt for use is sodium glycocholate.

Examples of lecithin include, Phospholipon-H™ saturated phospholipid, Phospholipon-G™ unsaturated phospholipid, phosphatidylcholine, phosphatidyl serine, sphingomyelin, phosphatidylethanolamine, cephalin, and lysolecithin.

In one embodiment, a mixed micellar composition is provided comprising a pharmaceutical agent encapsulated in a mixture of micelles, wherein the micelles are formed by at least two different micelle-forming compounds in an aqueous solvent, each micelle comprising one or more micelle-forming compounds. In such a mixed micellar composition, at least two different micelles will be present. Thus, a first micelle-forming compound may comprise an alkali metal alkyl sulfate to form a first micelle-encapsulated pharmaceutical agent, and the second micelle-forming compound may comprise a polyoxyethylene ether to form a second micelle-encapsulated pharmaceutical agent. One or both of these micelles may include an additional micelle-forming compound, e.g. a bile acid or another micelle-forming compound, to yield first and second micelles comprising a different combination of micelle-forming compounds.

The present micellar composition comprises an amount of each of the one or more micelle-forming compounds of about 0.1 and 30 wt./wt. % of the total composition, for example, 1 to 10 wt/wt % of the total formulation, and preferably 2-5 wt/wt % of the total composition.

To aid in the formation of micelles, the composition additionally comprises a pharmaceutically acceptable edetate (a salt of ethylenediaminetetraacetic acid) in a concentration of from about 1 to 10 wt./wt. % of the total composition, and at least one alkali metal salicylate in a concentration of from 1 to 10 wt./wt. % of the total composition. In one embodiment, the edetate may be an alkali metal edetate, and preferably, the alkali metal edetate is selected from the group consisting of disodium edetate, dipotassium edetate, and combinations thereof. In one embodiment, the alkali metal salicylate is sodium salicylate. In other embodiments, the micelle-forming compounds, the edetate and the alkali metal salicylate are each in a concentration of from 2 to 5 wt./wt. % of the total composition.

The composition may also optionally comprise an isotonic agent to stabilize the micelles in solution. Examples of suitable isotonic agents include, but are not limited to, saccharides such as sorbitol and mannitol; polyhydric alcohols such as glycerin, polyglycerin, propylene glycol and the like; and dibasic sodium phosphate. Preferably, the isotonic agent is glycerin. Glycerin can function both as a micelle forming compound and an isotonic agent. Dibasic sodium phosphate functions as an isotonic agent and anti-bacterial. The concentration of the isotonic agent, if used, is between about 0.1 to 30% by wt of the total composition.

The micelles of the present composition generally provide nanonization of the pharmaceutical agent, and are of a size within the range of about 1 to 1000 nm (nanometers), preferably of a size within the range of about 10 to 500 nm, and more preferably of a size in the range of 10-100 nm.

The composition is not particularly restricted with respect to the pharmaceutical agent. Advantageously, the pharmaceutical agent is a macromolecular pharmaceutical agent having a molecular weight of at least about 1 kDa, preferably in the range of about 1 to 2000 kDa. Examples of pharmaceutical agents that may be incorporated in the present composition include, but are not limited to:

protein-based pharmaceutical agents such as insulin, heparin, low molecular weight heparin, hirulog, hirugen, huridine, interferons, interleukins, cytokines, mono- and poly-clonal antibodies, immunoglobins, chemotherapeutic agents, vaccines, glycoproteins, bacterial toxoids, hormones, calcitonins, growth factors such as insulin like growth factor (IGF), glucagon like peptides (GLP-1), large molecule antibiotics, protein-based thrombolytic compounds, erythropoietin and platelet inhibitors;

nucleic acid-based pharmaceutical agents such as DNA, RNA, gene therapeutics and antisense oligonucleotides.

antimicrobial agents, such as triclosan, cetyl pyridium chloride, domiphen bromide, quaternary ammonium salts, zinc compounds, sanguinarine, fluorides, alexidine, octonidine, EDTA, and the like;

non-steroidal anti-inflammatory drugs, such as aspirin, acetaminophen, ibuprofen, ketoprofen, diflunisal, fenoprofen calcium, naproxen, tolmetin sodium, indomethacin, and the like;

anti-tussives, such as benzonatate, caramiphen edisylate, menthol, dextromethorphan hydrobromide, chlophedianol hydrochloride, and the like;

decongestants, such as pseudoephedrine hydrochloride, phenylepherine, phenylpropanolamine, pseudoephedrine sulfate, and the like;

anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like;

expectorants, such as guaifenesin, ipecac, potassium iodide, terpin;

anti-diarrheals, such a loperamide, and the like;

$H_2$-antagonists, such as famotidine, ranitidine, and the like;

proton pump inhibitors, such as omeprazole and lansoprazole;

nonselective CNS depressants, such as aliphatic alcohols, barbiturates and the like;

nonselective CNS stimulants such as caffeine, nicotine, strychnine, picrotoxin, pentylenetetrazol and the like;

drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like;

antiparkinsonism drugs such as levodopa, amantadine and the like;

analgesic-antipyretics such as salycilates, phenylbutazone, indomethacin, phenacetin and the like;

psychopharmacological drugs such as chlorpromazine, methotrimeprazine, haloperidol, clozapine, reserpine, imipramine, tranylcypromine, phenelzine, lithium and the like;

hypnotics, sedatives, antiepileptics, awakening agents;

vitamins and minerals;

amino acids and peptides;

sildenafil citrate;

antidiabetic drugs, e.g. metformin, glyburide and insulin secretart agent, insulin stimulators, fat metabolizers, carbohydrates metabolizers, insulin, cholesterol lowering agents like statins, etc.

opioid analgesics such as alfentanil, allylprodine, alphaprodine, anileridine, benzylmorphine, bezitramide, buprenorphine, butorphanol, clonitazene, codeine, cocaine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazine, fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, diamorphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, mixed mu-agonists/antagonists, mu-antagonist combinations, mixtures of any of the foregoing, and the like. The opioid analgesic may be in the form of the free base, or in the form of a pharmaceutically acceptable salt, or in the form of a pharmaceutically acceptable complex; and cannibinoids.

The term "cannabinoid" is used herein to refer to a class of diverse chemical compounds that act on cannabinoid receptors in cells that repress neurotransmitter release in the brain. Cannibinoids include the endocannabinoids (produced naturally in the body by humans and animals, such as arachidonoyl-ethanolamide (anandamide), 2-arachidonoyl glycerol (2-AG) and arachidonyl glyceryl ether (noladin ether), the phytocannabinoids (found in cannabis and some other plants), synthetic cannabinoids (manufactured artificially), and functionally equivalent derivatives and analogues of any of these. Examples of cannabinoids include, but are not limited to, cannabidiol (CBD), cannabidiol acid (CBDA), cannabinol (CBN), cannabigerol (CBG), cannabigerol acid (CBGA), cannabidivarin (CBDV), cannabidivarin acid (CBDVA), cannabinovarin (CBNV), cannabigerovarin (CBGV), cannabichromene (CBC), naphthoylindoles such as JWH-018, JWH-073, JWH-398, JWH-200, JWH-081, 4-methyl-JWH-073, JWH-015, JWH-122, JWH-220, JWH-019, JWH-007; phenylacetylindoles such as JWH-250 and JWH-203; benzoylindoles such as RCS-4, AM-694 and WIN 48,098; cyclohexylphenoles such as CP 47,497-C8 and CP 47,497; and HU-210. FIG. 1 illustrates chemical structures of a number of these compounds. Cannibinoids also include tetrahydrocannabinoid and analogs thereof, namely, delta-9 tetrahydrocannabinol (THC) and functionally equivalent compounds, including analogs and derivatives thereof such as delta-8 tetrahydrocannabinol (D8-THC), tetrahydrocannabinol acid (THCA), tetrahydrocannabivarin (THCV), tetrahydrocannabivarin acid (THCVA), nabilone, rimonabant (SR141716), JWH-018, JWH-073, CP-55940, dimethylheptylpyran, HU-210, HU-331, SR144528, WIN 55,212-2, JWH-133, levonantradol and AM-2201. The term "functionally equivalent" as it relates to analogs and derivatives of a cannibinoid refers to compounds which exhibit the same or similar therapeutic effect, e.g. at least about 50% of the activity of the cannibinoid from which it is derived.

Cannabinoids may be extracted from the cannabis plant using methods well-established in the art. Many of the cannibinoids may also be prepared using standard chemical synthetic methods. Some of these compounds are also commercially available.

As will be understood by one skilled in the art, the pharmaceutical agent may be provided in the form of a pharmaceutically acceptable salt. A "pharmaceutically acceptable salt" refers to a salt that retains the desired biological activity of the parent compound and does not impart any undesired toxicological effects (see e.g., Berge, S. M. et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as those derived from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amities, such as N,N'-dibenzylethylenediamine, N-methylglucamine, chloroprocaine, choline, diethanolamine, ethylenediamine, procaine and the like. Other salts include sulfate, citrate, phosphate and tartrate. Examples of opioid salts include morphine hydrochloride, morphine sulfate and fentanyl citrate.

The amount of pharmaceutical agent in the present micellar composition will vary with the particular pharmaceutical agent selected, and the intended mode of administration, among other factors. Typically, the present micellar composition will comprise the selected pharmaceutical agent in an amount between about 0.1 and 30 wt./wt. % of the total composition, more preferably, in an amount between about 0.1 and 10 wt./wt. % of the total composition.

The present micellar composition is prepared by:
i) admixing the selected pharmaceutical agent in a solvent with a first micelle-forming compound in an amount of from 1 to 10 wt./wt. % of the total composition, an alkali metal salicylate in an amount of from 1 to 10 wt./wt. % of the total composition, a pharmaceutically acceptable edetate in an amount of from 1 to 10 wt./wt. % of the composition, and optionally an isotonic agent, to form micelles; and
ii) optionally adding to the micellar composition a second micelle-forming compound in an amount of from 1 to 10 wt./wt. % of the total composition, and further optionally adding a third micelle-forming compound in an amount of from 1 to 10 wt./wt. % of the total composition, and mixing vigorously to form a mixed micellar composition, wherein the total amount of micelle-forming compounds, alkali metal salicylate, edetate and isotonic agent, is less than 50 wt./wt. % of the composition.

In one embodiment, the first micelle-forming compound is selected from the group consisting of a polyoxyethylene ether, ester or alcohol; an alkali metal alkyl sulfate; a bile acid; and mixtures thereof; and the second micelle-forming compound is selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, trihydroxy oxo cholanylglycine, glycerin, polyglycerin, lysine, polylysine, triolein and mixtures thereof.

In another embodiment, the third micelle-forming compound is selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, trihydroxy oxo cholanylglycine, glycerin, polyglycerin, lysine, polylysine, triolein and mixtures thereof, and is different from the second micelle-forming compound.

In another embodiment, the first micelle-forming compound is an alkali metal alkyl sulfate, and the second micelle-forming compound is a mixture of a polyoxyethylene ether and a bile salt. In another embodiment, the first micelle-forming compound is a mixture of an alkali metal alkyl sulfate and a polyoxyethylene ether, and the second micelle-forming compound is a bile acid or salt thereof.

In other embodiments, the first and second micelle-forming compounds are, respectively, sodium hyaluronate and phospholipon-H, or phospholipon-H and glycolic acid, or sodium hyaluronate and lecithin.

In yet other embodiment, the three micelle-forming compounds are trihydroxy oxo cholanyl glycine, polyoxyethylene ether and lecithin; or trihydroxy oxo cholanyl glycine, deoxycholate and glycerin; or polidocanol 9 lauryl ether, polylysine and triolein.

The micellar composition comprises a pharmaceutically acceptable solvent, i.e. a non-toxic solvent that is suitable for administration to a mammal with no unacceptable adverse effects. The solvent may be an aqueous or non aqueous solvent. A preferred solvent is water. Other suitable solvents include alcohol solutions, especially ethanol. A combination of water and ethanol is useful if the composition is to be formulated with a propellant for administration as an aerosol. The solvent comprises the balance of the composition to yield 100 wt./wt. %. A portion of the solvent may be used initially to solubilize the pharmaceutical agent prior to the addition of the micelle-forming compounds. The resulting micellar composition has a pH in the range of 5 to 8, and preferably, a pH between about 6.0 and 7.0. As one of skill in the art will appreciate, pH may be adjusted up or down by addition of a suitable base (e.g. sodium hydroxide) or acid (e.g. hydrochloric acid), respectively.

The micellar composition may optionally contain a stabilizer and/or a preservative. Phenolic compounds, i.e. compounds comprising one or more hydroxyl groups on a benzyl ring, are particularly suited for this purpose as they not only stabilize the composition, but they also protect against bacterial growth and enhance absorption of the composition. Preferred phenolic compounds include phenol and methyl phenol (also known as m-cresol), and mixtures thereof.

The micellar composition may also comprise one or more of the following additional additives: inorganic salts, antioxidants, protease inhibitors, colorants and flavoring agents. Non-limiting examples of inorganic salts include sodium, potassium, calcium and zinc salts, especially sodium chloride, potassium chloride, calcium chloride, zinc chloride and sodium bicarbonate. Examples of antioxidants include tocopherol, deteroxime mesylate, methyl paraben, ethyl paraben, ascorbic acid and mixtures thereof. Examples of protease inhibitors include but are not limited to bacitracin and bacitracin derivatives such as bacitracin methylene disalicylates, soybean trypsin, and aprotinin. Examples of flavoring agents include menthol, sorbitol and fruit flavors. Such additional additives may comprise between about 0.1 and 5 wt./wt. % of the composition. Bacitracin and its derivatives preferably comprise between 1.5 and 2 wt./wt. % of the total composition, while soyabean trypsin and aprotinin preferably comprise between about 1 and 2 wt./wt. % of the total composition. During the process of preparing the micellar composition, the additional additives may be added with either the first or second micelle-forming compound.

The micellar compositions of the present invention may be stored at room temperature or below. Storage of the composition at 4° C. or less is preferable to prevent degradation of the pharmaceutical agent and, thereby, to provide an extended shelf life.

The present composition may be formulated for administration by a desired route of administration selected from parental routes such as intravenous, intramuscular, intradermal, intraperitoneal, subcutaneous, spinal, intraarterial, intrathecal, intracapsular, intraorbital, intracardiac, transtracheal, subcuticular, intraarticular, subcapsular, subarachnoid, intraspinal, epidural and infrasternal injection and infusion; and non-parenteral routes such as topical, epidermal or mucosal routes of administration, for example, intranasally, orally, vaginally, rectally, sublingually, transdermally or topically.

In one embodiment, the composition is provided in the form of a rapidly dissolving orally administrable formulation. The mucosal membranes of the mouth contain a thin protective membrane through which the pharmaceutical agent-containing micelles of the present composition can readily traverse since they are generally smaller than the pores of the membrane. The mucosal membranes is composed of many superficial blood vessels in direct contact with the circulation. Thus, absorption of the micelles in the present formulation into the oral mucosa enables rapid absorption into the blood stream, e.g. within about 5-7 minutes of taking the dose.

The orally administrable formulation may comprise at least one physiologically acceptable film forming agent such as pullulan, methyl cellulose, ethyl cellulose, sodium carboxymethyl cellulose, hydroxypropylmethyl cellulose, hydroxyethyl cellulose, hydroxypropyl cellulose, carboxymethyl cellulose, polyvinyl pyrrolidone, methacrylic acid polymers, methacrylic acid copolymers, acrylic acid polymers, acrylic acid copolymers, polyacrylamides, polyalkylene oxides, carrageanan, polyvinyl alcohol, sodium alginate, polyethylene glycol, polyacrylic acid, glycolide, polylactide, methylmethacrylate copolymer, carboxyvinyl polymer, amylose, high amylose starch, hydroxypropylated high amylose starch, alginic acid, pea starch, dextrin, pectin, chitin, chitosan, levan, elsinan and mixtures thereof. Secondary film forming agents may be added to the formulation to optimize wafer characteristics such as tensile strength, stability, flexibility and brittleness including agents such xanthan gum, tragacanth gum, guar gum, locust bean gum, acacia gum, arabic gum, collagen, gelatin, zein, gluten, soy protein isolate, whey protein isolate, casein and mixtures thereof. Generally, the wafer comprises 5 to about 80% by wt of one or more film forming agents.

In one embodiment, the orally administrable formulation comprises at least about 30 to about 80 wt % film forming agent, such as pullulan, or a mixture of pullulan with one or more other film forming agents such as polyvinyl alcohol, carrageenan, guar gum, xanthan gum and locust bean gum. In one embodiment, the formulation comprises PEG in an amount of less than about 5 wt %.

In another embodiment, the orally administrable formulation comprises a mixture of sodium carboxymethylcellulose and hydroxypropyl-cellulose or methyl cellulose as the film-forming agents. The ratio of sodium carboxymethylcellulose to hydroxypropyl cellulose (or methylcellulose) used to make the formulation is chosen to yield the desired dissolution time and mouth-feel for the film and to further impart acceptable product handling characteristics. While not wishing to be bound by theory, it is believed that the carboxymethyl cellulose imparts ease of dissolution in the mouth and robust mouthfeel, while hydroxypropyl cellulose (or methyl cellulose) imparts improved mechanical strength, particularly improved tear strength. The formulation may include from about 5 wt % to 75 wt %, particularly from about 15 to 50 wt %, based on the weight of the formulation of sodium carboxymethylcellulose and hydroxypropyl-cellulose (or methylcellulose). Exemplary amounts of sodium carboxymethylcellulose range from about 7 to 40 wt % and exemplary amounts of hydroxylpropyl methyl cellulose range from 3.5 to 14 wt %. Exemplary amounts of hydroxypropyl cellulose ranges from about 10 to 40 wt %. Pectin may also be combined with carboxymethylcellulose and hydroxypropyl-cellulose or methyl cellulose in an amount ranging from about 4 to 25 wt %.

The orally administrable formulation may also include one or more adjuvants selected from the group consisting of: a plasticizing agent, a flavoring agent, a sulfur precipitating agent, a saliva stimulating agent, a cooling agent, a surfactant, a stabilizing agent, an emulsifying agent, a thickening agent, a binding agent, a coloring agent, a sweetener, flavouring agent, cooling sensation agent, taste receptor blocker and a fragrance.

Exemplary sweeteners include dextrose, lactose, fructose, mannitol, sucrose, trehalose, sucralose, xylitol, mannitol, aspartame, saccharin, sorbitol, sodium saccharin, sodium cyclamate, acesulfame, honey, isomalt, maltodextrin, dextrin, dextrates and mixtures thereof. Particularly preferred sweeteners include isomalt, sucralose, aspartame, saccharine, acesulfame or mixtures thereof. In one embodiment, isomalt is used as an adjunct sweetener to a primary sweetener, particularly a primary sweetener selected from one or more of sucralose, aspartame, saccharine and acesulfame. Exemplary flavouring agents include menthol and sorbitol.

The orally administrable formulation may include an anti-microbial agent. In one embodiment, the formulation comprises one or more essential oils that confer antimicrobial properties. Preferably, the amount of a selected essential oil for use in the formulation is sufficient to provide anti-microbial efficacy while not changing the physical characteristics of the wafer, e.g. an amount ranging from 0.01 to 15 wt %. Generally, an oil such as thymol, methyl salicylate and/or eucalyptol may be present in an amount of about 0.01 to about 4 wt % of the formulation, preferably about 0.50 to about 3.0 wt % of the formulation, and even more preferably from about 0.70 to about 2.0 wt % of the formulation. Menthol may be added in an amount ranging from about 0.01 to about 15 wt % of the formulation, preferably about 2.0 about 10 wt %, and even more preferably from about 3 to about 9 wt % of the formulation. The appropriate amount of a selected anti-microbial oil in the formulation can readily be determined by one of skill in the art, and may exceed the foregoing amounts.

The oral formulation may include an antioxidant is selected from the group consisting of: tocopherol, deteroxime mesylate, methyl paraben, ethyl paraben, ascorbic acid and mixtures thereof. A preferred antioxidant is tocopherol.

The oral formulation may include a protease inhibitor such as bacitracin, soyabean trypsin, aprotinin and bacitracin derivatives, e.g. bacitracin methylene disalicylate.

Saliva stimulating agents may be added to the oral formulation according to the present invention. Examples of saliva stimulating agents include food acids such as citric, lactic, malic, succinic, ascorbic, adipic, fumaric and tartaric acids. Preferred food acids are citric, malic and ascorbic acids. The amount of saliva stimulating agents suitable for inclusion in the present formulation may range from about 0.01 to about 12 wt %, preferably about 1 wt % to about 10 wt %.

Plasticizing agents may be included in the oral formulation to attain desired flexibility and mold-releasing properties. Suitable plasticizing agents include, for example, triacetin, monoacetin and diacetin. Plasticizing agent may be added to the formulation in an amount ranging from about 0 to about 20 wt %, preferably about 0 to about 2 wt % of the formulation.

Cooling agents may be added to the formulation to increase the boiling point of the gel and thereby prevent bubble formation. An example of a cooling agent that may be added to the formulation is monomenthyl succinate, in an amount ranging from about 0.001 to about 2.0 wt %, preferably about 0.2 to about 0.4 wt % of the formulation. Other suitable cooling agents include WS3, WS23, Ultracool II and the like.

To provide the oral formulation in chewable form, guar gum, powdered acacia, carrageenin, beeswax and xanthan gum are added in a suitable amount.

Various methods for making such an orally administrable formulation may be applied, including the method described in U.S. Pat. No. 8,623,401, the contents of which are incorporated herein by reference. Generally, the selected film-forming agents are dissolved in an aqueous solution with the present pharmaceutical agent-containing micellar composition, including any desired adjuvants, to form a gel. The gel is then formed into a thin layer and exposed to a plurality of heating and/or cooling cycles, for example, for a period of no more than about 3 minutes, to result in a product that can be formed into suitable dosage forms, such as wafers. The wafer generally exhibits a very high rate of dissolution, e.g. a dissolution rate of at least about 2 milligrams/sec, in an aqueous environment. Due to its high rate of dissolution, the wafer accordingly exhibits a very desirable rate of delivery of drug, i.e. $T_{max}$, the amount of time following administration of the wafer for the drug it contains to reach its maximum plasma concentration. For example, $T_{max}$ for delivery of the present micellar composition may be about 10 minutes, and preferably less than 10 minutes, e.g. 8 minutes or less.

In another embodiment, an orally administrable wafer may be prepared by dissolving the selected film-forming agent(s) in an aqueous solution in combination with the present pharmaceutical agent-containing micellar composition and any desired adjuvants, with stirring and heat, to form a gel. The gel is then spread as a thin layer, e.g. about 10 microns or less, and allowed to cool. Wafers may then be formed therefrom.

In another embodiment, the present micellar composition may be formulated for application topically as a cream, lotion or ointment. For such topical application, the composition may include an appropriate base such as a triglyceride base. Such creams, lotions and ointments may also contain a surface active agent and other cosmetic additives such as skin softeners (e.g. aloe vera) and the like as well as fragrance. As will be appreciated by one of skill in the art, a topical formulation may also be administered via a transdermal patch, bandage or cloth. Aerosol formulations, for example, for nasal delivery, may also be prepared in which suitable propellant adjuvants are used. Compositions of the present invention may also be administered as a bolus, electuary, or paste. Compositions for mucosal administration are also encompassed, including oral, nasal, rectal or vaginal administration for the treatment of infections which affect these areas. Such compositions generally include one or more suitable non-irritating excipients or carriers comprising, for example, cocoa butter, polyethylene glycol, a suppository wax, a salicylate or other suitable carriers. Other adjuvants, such as preservatives, anti-microbial agents and the like, may also be added to the micellar composition regardless of how it is to be administered which, for example, may aid to extend the shelf-life thereof.

Topical formulations may be prepared by combining the present micellar composition with one or more transcutaneous carriers selected from the group consisting of water, short carbon chain alcohols such as tert-butyl alcohol, tert-butyl alcohol, 1,3-butanediol, tert-amyl alcohol, 3-methyl-3-pentanol, ethchlorvynol, 1-octanol (capryl alcohol), pelargonic alcohol (1-nonanol), 1-decanol (decyl alcohol, capric alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol), stearyl alcohol (1-octadecanol), nonadecyl alcohol (1-nonadecanol), arachidyl alcohol (1-eicosanol), heneicosyl alcohol (1-heneicosanol), behenyl alcohol (1-docosanol), erucyl alcohol (cis-13-docosen-1-ol), lignoceryl alcohol (1-tetracosanol), ceryl alcohol (1-hexacosanol), 1-heptacosanol, montanyl alcohol, cluytyl alcohol, or 1-octacosanol, 1-nonacosanol and myricyl alcohol, melissyl alcohol, or 1-triacontanol, or glycerol; dimethysulfoxide, and its derivatives; film forming agents as described above, surfactant such as an alkali metal edidate, e.g. sodium lauryl sulfate, polyoxyethylene lauryl ether and derivatives; emulsifiers such as sodium lauryl sulfate, polyoxyethylene (40) stearate, stearic acid and lecithin; anti-inflammatory agents such as niacinamide; skin conditioning/softening agents and emollients such as aloe vera, linoleic acid, vitamin E and the acetate thereof, and crodamol sts; absorption enhancers such as polyoxyethylene compounds and/or derivatives; anti-microbial agents; preservatives and stabilizers (such as phenoxyethanol) and excipients such as polyethylene glycol, polypropylene glycol, glycerin, oils such as mineral oil, olive oil, sesame oil, castor oil and the like, and mixtures thereof. As one of skill in the art will appreciate, the topical formulation may include additional adjuvants and excipients which enhance the utility of the formulation for topical use.

The components of the topical formulation may be combined with the micellar composition in phases to result in a formulation suitable to topical administration. For example, a first phase (phase A) including transcutaneous carriers such as water and/or an alcohol, an emulsifier (e.g. an alkali metal edidate or sodium lauryl sulfate), and skin agents (e.g. aloe compounds) may be combined. A second phase (phase B) may include a carrier (e.g. alcohol), oils, absorption enhancer and/or emollient. Additional phases may include other suitable adjuvants including surfactants, emollients, absorption enhancers, oils, anti-inflammatory agents, skin agents, stabilizers and antimicrobial agents (e.g. germicides, biocides and the like such as diocide). Thus, a first additional phase may include one or more skin agents (e.g. linoleic acid, acetate compounds), oils and absorption enhancers; a second additional phase may include one or more emulsifiers, phospholipids and absorption enhancers; and another additional phase may include one or more anti-microbial agents and stabilizers.

The transcutaneous carrier or mixture of carriers is present in the topical formulation in an amount of up to about 50-60% by wt of the formulation. Other components are present in an amount in the range of about 1-10% by wt; however, as one of skill in the art will appreciate amounts of such other components outside of this range is acceptable as well, particularly if there is a combination of like components, e.g. two or more surfactants, two or more emollients, two or more skin agents, etc.

Embodiments of the invention are described in the following examples which are not to be construed as limiting.

Example 1—Nanonized Wafer Preparation

In a 250 mL capacity glass beaker was added 5 g sodium lauryl sulfate, 5 g sodium salicylate and 2.5 g edetate. The beaker was placed on a hot plate with a magnetic stirrer. To this dry powder mixture was added 100 mL distilled water and the mixture was stirred, using the magnetic stir bar, at a medium speed until all the powder was dissolved. This buffer solution was stored in a clean glass bottle at room temperature (pH 6.5).

A 2% menthol solution was then prepared from 100 mg menthol crystals, dissolved in 5 mL ethanol. To this solution was added 5 mg FD &C blue dye. The solution was stirred for 10 minutes and stored in a glass bottle at room temperature.

A mixed micellar cannabinoid solution was then prepared in a 50 mL glass beaker, into which was placed 100 mg of phosphatidylcholine (Sigma, type I-EH, hydrogenated). To this powder was added 10 mL of isopropyl alcohol. The mixture was stirred at a high speed (1000 rpm) for about 10 minutes to ensure complete dissolution of the phosphatidylcholine. To this solution was added the cannabinoid solution (THC 5%+CBD 5% in a 50:50 mixture water and ethanol) (30% by wt) very slowly, drop wise, using a glass dropper, with continuous stirring at a high speed. The solution was stirred continuously for another 30 minutes at a high speed to ensure uniform micellar particle size distribution. To this solution was added 1 mL of the 2% menthol solution and dye solution. The semi-clear, translucent, light blue solution was stored in a clean glass bottle. The solution had a pH of 6.5 (micellar composition F).

Figure 2:
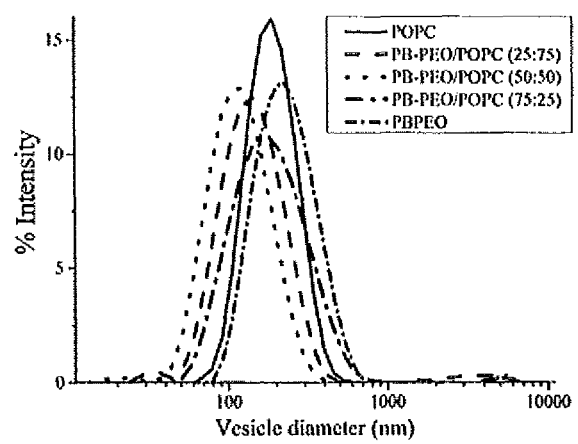
FIG. 2 illustrates particle size distribution within a nanonized cannabinoid solution comprising different ratios of first and second micelle-forming compounds.

A similar micellar composition was prepared using sodium lauryl sulfate-polyoxy ethylene and phosphatidylcholine (POPC) as micelle-forming compounds at various ratios, to form both mixed and non-mixed micellar compositions. Particle size distribution of the micellar composition was determined using laser light scattering, FIG. 2 shows that particle size distribution is within the range of 50-1000 nm for each combination.

The following method was used to prepare a wafer. Amounts of each component are set out in Table 1 below.

TABLE 1

Wafer components and amounts

| INGREDIENT | WEIGHT (grams) |
|---|---|
| Xanthan Gum | 1.076 |
| Locust Bean Gum | 0.215 |
| Carrageenan | 1.073 |
| Pullulan | 51.00 |
| Deionized Water | 31.258 |
| Na Lauryl Sulfate | 3 |
| Phosphatidyl choline | 3 |
| Glycerine | 3 |
| Mineral Oil | 3 |
| Polysorbate 80 | 0.4 |
| Atlas 3000/Atmos300 | 0.4 |

The film-forming ingredients (e.g., xanthan gum, locust bean gum, carrageenan and pullulan) are mixed and hydrated in hot purified water to form a gel and stored in a refrigerator overnight at a temperature of approximately 4° C. to form preparation A;

The coloring agent(s) (selected food dye) and sweetener (sorbitol) are added in an amount of less than 1% by wt of each and dissolved in purified water to form preparation B;

Preparation B is added to preparation A and mixed well to form preparation C;

The flavoring agent and the oils (e.g. thymol, methyl salicylate, eucalyptol and menthol) in an amount of less than 1% by wt of each are mixed to form preparation D;

The polysorbate 80 and Atmos 300 are added to preparation D and mixed well to form preparation E;

Na Lauryl sulfate, phosphatidyl choline and glycerine were added to preparation E at 60° C. and mixed well to form micellar preparation F; and Preparation F was added to preparation C and mixed well to form preparation G. Preparation G is poured on a mold and cast to form a film of a desired thickness. The molds containing the film forming solutions were put on a conveyor belt and then passed through a special microwave chamber. Five microwave chambers were utilized for the quick film formation. Each microwave chamber had dimensions of about 14"×11"×9" and were programmed to heat the solution for 10 seconds. The conveyor belt speed was adjusted to move the molds slowly enough to complete the 10 seconds heating and cooling cycles. Specifically, the belt speed was adjusted to move the molds about 1 foot per 7 seconds (approximately 8 feet travel time) to provide sufficient time for the microwaves to complete one heating cycle. The microwaves were stationed about 18" away from each other. The whole chamber containing the microwave was designed to maintain the temperature of 37° C. with constant positive air flow. The wafers thus made were stored at room temperature. The whole cycle of making wafers of 1.5" long, 0.5 inch wide and 0.1 mm thick was about 90 seconds in total.

Figure 3:
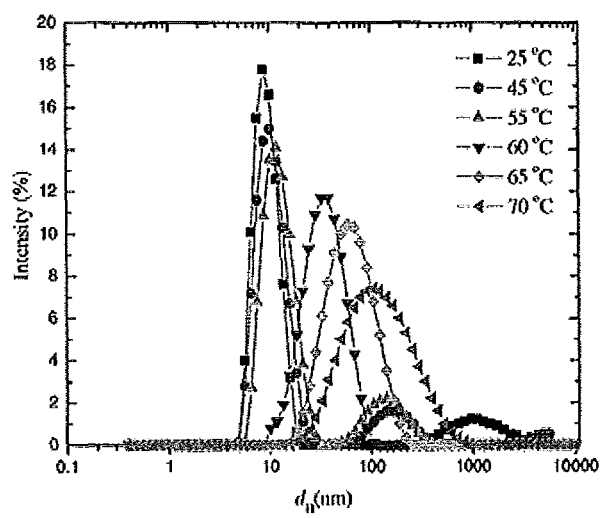
FIG. 3 illustrates particle size distribution within a wafer comprising the nanonized cannabinoid solution at various temperatures.
Figure 4:
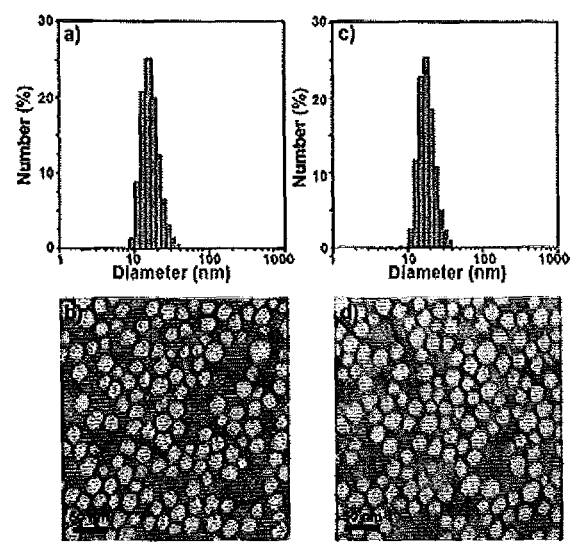
FIG. 4 graphically illustrates the results of an SEM analysis of particles within a wafer containing nanonized cannibinoid.

The resulting wafer was dissolved in water, and particle size within the wafer was determined. As shown in FIG. 3, particle size of the micellar composition is retained, and it is shown that an increase in temperature increases particle size distribution within the range of 1-1000 nm. SEM analysis of the wafer also shows retention of particle size in the range of 10-100 nm at the optimum temperature of about 55° C. (FIG. 4).

The invention claimed is:

1. An orally administrable composition in the form of a wafer comprising: i) at least one physiologically acceptable film forming agent in an amount ranging from about 30 to 80% by wt. in a pharmaceutically acceptable aqueous solvent combined with ii) a micellar composition comprising a cannabinoid encapsulated in micelles of 50-1000 nm in size formed by micelle-forming compounds, in a pharmaceutically acceptable aqueous solvent, wherein the at least one physiologically acceptable film forming agent comprises pullulan, and the micelle-forming compounds comprise sodium lauryl sulfate, a bile acid and glycerine, and wherein the wafer is formed by applying cycles of heating and cooling.

2. The orally administrable composition of claim 1, wherein the composition further comprises one or more micelle-forming compounds selected from the group consisting of polyoxyethylene ethers, esters or alcohols; phosphatidylcholine; lecithin, hyaluronic acid, pharmaceutically acceptable salts of hyaluronic acid, octylphenoxypolyethoxyethanol, glycolic acid, lactic acid, oleic acid, linoleic acid, linolenic acid, monoolein, monooleates, monolaurates, borage oil, evening of primrose oil, chamomile extract, cucumber extract, menthol, trihydroxy oxo cholanylglycine, polyglycerin, lysine, polylysine, triolein, polidocanol alkyl ethers, and mixtures thereof.

3. The orally administrable composition of claim 2, further comprising a micelle-forming compound selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, trihydroxy oxo cholanylglycine, polyglycerin, lysine, polylysine, triolein and mixtures thereof.

4. The orally administrable composition of claim 1, wherein each micelle-forming compound, and an isotonic agent, are present in an amount in the range of from 1 to 10 wt./wt. % of the total composition, and the total amount of the micelle-forming compounds and the isotonic agent is less than 50 wt./wt. % of the composition.

5. The orally administrable composition of claim 1, wherein the cannabinoid is selected from the group consisting of cannabidiol (CBD), cannabidiol acid (CBDA), cannabinol (CBN), cannabigerol (CBG), cannabigerol acid (CBGA), cannabidivarin (CBDV), cannabidivarin acid (CBDVA), cannabinovarin (CBNV), cannabigerovarin (CBGV) and cannabichromene (CBC), delta-9 tetrahydrocannabinol (THC), delta-8 tetrahydrocannabinol (D8-THC), tetrahydrocannabinol acid (THCA), tetrahydrocannabivarin (THCV), tetrahydrocannabivarin acid (THCVA), and mixtures thereof.

6. The orally administrable composition of claim 1, wherein the at least one physiologically acceptable film forming agent comprises pullulan and an additional film forming agent selected from the group consisting of methyl cellulose, ethyl cellulose, sodium carboxymethyl cellulose, hydroxypropylmethyl cellulose, hydroxyethyl cellulose, hydroxypropyl cellulose, carboxymethyl cellulose, polyvinyl pyrrolidone, methacrylic acid polymers, methacrylic acid copolymers, acrylic acid polymers, acrylic acid copolymers, polyacrylamides, polyalkylene oxides, carrageanan, polyvinyl alcohol, sodium alginate, polyethylene glycol, polyacrylic acid, glycolide, polylactide, methylmethacrylate copolymer, carboxyvinyl polymer, amylose, high amylose starch, hydroxypropylated high amylose starch, alginic acid, pea starch, dextrin, pectin, chitin, chitosan, levan, elsinan and mixtures thereof.

7. The orally administrable composition of claim 6, wherein the additional film forming agent is selected from the group consisting of xanthan gum, tragacanth gum, guar gum, locust bean gum, acacia gum, arabic gum, collagen, gelatin, zein, gluten, soy protein isolate, whey protein isolate, casein and mixtures thereof.

8. The orally administrable composition of claim 6, wherein the at least one physiologically acceptable film forming agent comprises a mixture of pullulan with one or more additional film forming agents selected from polyvinyl alcohol, carrageenan, guar gum, xanthan gum and locust bean gum.

9. The orally administrable composition of claim 6, additionally comprising one or more of: a plasticizing agent, a flavoring agent, a sulfur precipitating agent, a saliva stimulating agent, a cooling agent, a surfactant, a stabilizing agent, an emulsifying agent, a thickening agent, a binding agent, a coloring agent, a sweetener, and a fragrance.

10. The orally administrable composition of claim 1, wherein the composition exhibits a Tmax of the cannabinoid on administration to a patient of less than about 7 minutes.

11. A method of preparing the orally administrable composition of claim 1 comprising the cannabinoid of claim 1, comprising the steps of: i) mixing the cannabinoid in a solvent together with the micelle-forming compounds of claim 1, with an isotonic agent, to form a micellar composition, wherein the total amount of the micelle-forming compounds, and the isotonic agent, is less than 50 wt./wt. % of the composition; and iii) combining the micellar composition with the at least one physiologically acceptable film forming agent, pullulan, in an aqueous solvent to form a gel, spreading the gel into a thin layer and allowing the gel to set, by applying cycles of heating and cooling.

12. The orally administrable composition of claim 1, wherein the micelles are of a size within the range of about 50 to 500 nm.

13. The orally administrable composition of claim 1, wherein the bile acid is selected from the group consisting of cholic acid, deoxycholic acid, glycocholic acid, chenodeoxycholic acid, taurocholic acid, glycodeoxycholic acid, taurodeoxycholic acid, salts thereof and mixtures thereof.

14. The method of claim 11, wherein the at least one physiologically acceptable film forming agent comprises a mixture of pullulan with one or more additional film forming agents selected from polyvinyl alcohol, carrageenan, guar gum, xanthan gum and locust bean gum.

* * * * *